United States Patent [19]

Vogelbacher et al.

[11] Patent Number: 5,290,755
[45] Date of Patent: Mar. 1, 1994

[54] SALICYLIC ACID DERIVATIVES AS SELECTIVE HERBICIDES

[75] Inventors: Uwe J. Vogelbacher; Joachim Rheinheimer, both of Ludwigshafen; Thomas Saupe, Sandhausen; Norbert Meyer, Ladenburg; Matthias Gerber, Mutterstadt; Karl-Otto Westphalen, Speyer; Helmut Walter, Obrigheim, all of Fed. Rep. of Germany

[73] Assignee: BASF Aktiengesellschaft, Ludwigshafen, Fed. Rep. of Germany

[21] Appl. No.: 924,491

[22] Filed: Aug. 4, 1992

[30] Foreign Application Priority Data

Aug. 10, 1991 [DE] Fed. Rep. of Germany ....... 4126936

[51] Int. Cl.$^5$ ............... C07D 239/52; C07D 239/60; C07D 239/34; A01N 43/54
[52] U.S. Cl. .................. 504/242; 504/243; 504/225; 504/196; 504/197; 544/123; 544/243; 544/300; 544/301; 544/302; 544/312; 544/310; 544/314; 544/316; 544/318
[58] Field of Search ............ 71/92, 86, 90; 544/122, 544/123, 243, 301, 302, 312, 314, 316, 318, 58.6, 55, 3, 96, 63, 300; 504/242, 243, 225, 196, 197

[56] References Cited

U.S. PATENT DOCUMENTS 5,085,686  2/1992  Vogelbacher et al. .............. 71/92

FOREIGN PATENT DOCUMENTS 2029027  5/1991  Canada .

*Primary Examiner*—John M. Ford
*Attorney, Agent, or Firm*—Keil & Weinkauf

[57] ABSTRACT

Salicylic acid derivatives and sulfur analogs thereof of the formula I,

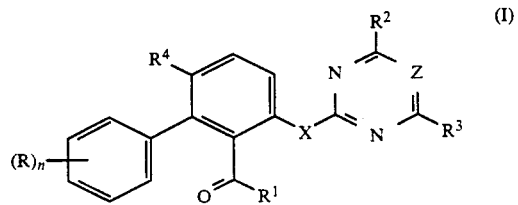

wherein the substituents are herein below defined.

10 Claims, No Drawings

SALICYLIC ACID DERIVATIVES AS SELECTIVE HERBICIDES

The present invention relates to salicylic acid derivatives and sulfur analogs thereof of the formula I

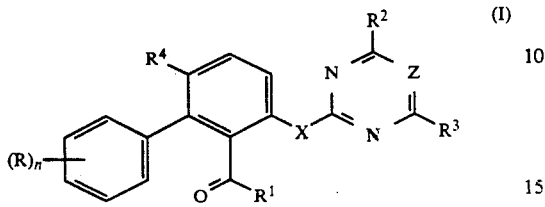

where
R is halogen, $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio; n is 1, 2 or 3 or, in the case of halogen as substituents, 1, 2, 3, 4 or 5,
$R^1$ is a radical

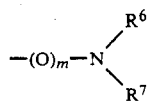

where m is 0 or 1 and $R^6$ and $R^7$ have the following meanings:
hydrogen;
$C_1$-$C_6$-alkyl, $C_3$-$C_6$-alkenyl or $C_3$-$C_6$-alkynyl, where these radicals may each carry from one to five halogen atoms and/or one or two of the following groups: $C_1$-$C_6$-alkoxy, $C_3$-$C_6$-alkenyloxy, $C_3$-$C_6$-alkynyloxy, $C_1$-$C_6$-alkylthio, $C_3$-$C_6$-alkenylthio, $C_3$-$C_6$-alkynylthio, $C_1$-$C_6$-haloalkoxy, cyano, $C_1$-$C_6$-alkylcarbonyl, $C_3$-$C_6$-alkenyloxycarbonyl, $C_3$-$C_6$-alkynylcarbonyl, $C_1$-$C_6$-alkoxycarbonyl, $C_3$-$C_6$-alkenyloxycarbonyl, $C_3$-$C_6$-alkynyloxycarbonyl, bis-$C_1$-$C_6$-dialkylamino, $C_3$-$C_6$-cycloalkyl or unsubstituted or substituted phenyl;
unsubstituted or substituted $C_3$-$C_6$-cycloalkyl;
unsubstituted or substituted phenyl; or
$R^6$ together with $R^7$ forms an unsubstituted or substituted $C_4$-$C_7$-alkylene chain in which a $CH_2$ group may be replaced by oxygen, sulfur or —NH; or
$R^1$ is a group

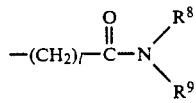

where $R^8$ and $R^9$ are each hydrogen, $C_1$-$C_6$-alkyl, $C_3$-$C_6$-alkenyl or $C_3$-$C_6$-alkynyl and l is 1, 2, 3 or 4; or
a group

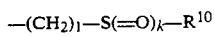

where $R^{10}$ is $C_1$-$C_6$-alkyl, $C_3$-$C_6$-alkenyl or $C_3$-$C_6$-alkynyl, l is 1, 2, 3 or 4 and k is 0, 1 or 2; or
$R^1$ is a radical

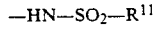

where $R^{11}$ is $C_1$-$C_6$-alkyl or phenyl which in turn may carry from one to four of the following substituents: halogen, nitro, cyano or $C_1$-$C_6$-alkyl;
a radical $OR^5$, where $R^5$ is an unsubstituted or substituted 5-membered aromatic heterocyclic structure which is bonded via a nitrogen atom and has from one to four nitrogen atoms in the ring; or
a radical

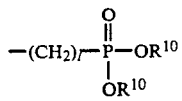

where $R^{10}$ and l have the abovementioned meanings, the expression unsubstituted or substituted in the above definitions meaning that the groups designated in this manner may carry one or more of the following substituents:
halogen, nitro, cyano, $C_1$-$C_6$-alkyl, $C_1$-$C_6$-haloalkyl, $C_1$-$C_6$-alkoxy or $C_1$-$C_6$-alkylthio
$R^2$ and $R^3$ are each $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio;
$R^4$ is hydrogen, halogen, nitro, $C_1$-$C_4$-alkyl, cyano or $C_1$-$C_4$-haloalkyl;
X is oxygen or sulfur, and
Z is nitrogen or the methine group.

EP-A 426 476 describes a herbicidal salicylic acid derivative having a phenyl substituent in the 6-position of the structure A.

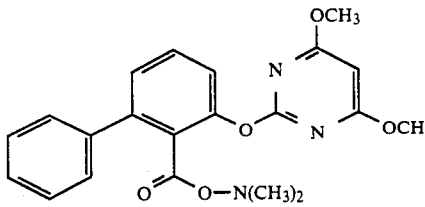

Example 44 from
EP-A 426 476

However, the selectivity of this compound is not always satisfactory and in particular is by no means sufficient when applied in cereal crops. Herbicidal salicylic acid derivatives are also described in EP-A 402 751, EP-A 346 789, EP-A 223 406, EP-A 249 708, EP-A 287 078 and EP-A 287 079.

It is an object of the present invention to provide salicylic acid derivatives which are effective in crop protection and have substantially better selectivity, in particular in cereal crops, than structurally similar compounds of the prior art.

We have found that this object is achieved by novel salicylic acid derivatives or sulfur analogs thereof having a substituted phenyl ring in the 6-position, as defined at the outset, which have excellent selectivity in cereal crops compared with the previously described compounds of the same type and furthermore have plant growth-regulating, fungicidal and/or nitrification-inhibiting properties.

The novel compounds are prepared as described in EP-A 426 476, either by converting an acid of the formula B (preparation described in EP-A 402 751)

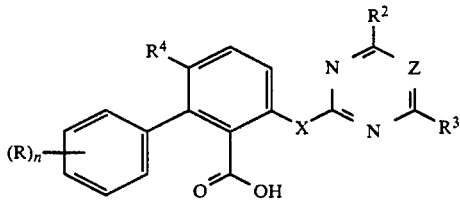

into an activated form and then reacting the latter with a hydroxylamine derivative of the formula HO—NR$^6$R$^7$, a compound HOR$^5$ or a sulfonamide of the formula H$_2$N—SO$_2$—R$^{11}$ as described above, or by converting a salicylic acid of the formula C (preparation described in EP-A 402 751)

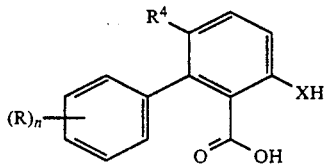

into an activated form, reacting the latter with a hydroxylamine derivative of the formula HO—NR$^6$R$^7$, a compound HOR$^5$ or a sulfonamide of the formula H$_2$N—SO$_2$—R$^{11}$ as described above to give a derivative of the formula D

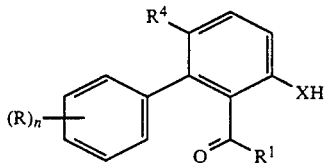

and then reacting the latter with a pyrimidine or triazine of the formula E

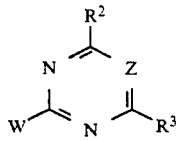

where W is a nucleofugic group, such as chlorine, methylsulfonyl or phenylsulfonyl with the aid of an inorganic or organic base.

With regard to the biological activity, preferred compounds I are those in which the substituents have the following meanings:

R is halogen, such as fluorine, chlorine, bromine or iodine, in particular chlorine or bromine;

C$_1$-C$_4$-alkyl, such as methyl, ethyl, propyl, 1-methylethyl, butyl, 1-methylpropyl, 2-methylpropyl or 1,1-dimethylethyl, preferably methyl or ethyl;

C$_1$-C$_4$-haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular difluoromethyl, trifluoromethyl, 2,2,2-trifluoroethyl or pentafluoroethyl;

C$_1$-C$_4$-alkoxy, such as methoxy, ethoxy or 1-methylethoxy;

C$_1$-C$_4$-haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy; and/or C$_1$-C$_4$-alkylthio, such as methylthio, ethylthio, propylthio, 1-methylethylthio, butylthio, 1-methylpropylthio, 2-methylpropylthio or 1,1-dimethylethylthio, in particular methylthio or ethylthio;

n is 1, 2 or 3 or, where R is halogen, furthermore 4 or 5;

R$^1$ is a radical

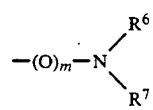

where m is 0 or 1 and R$^6$ and R$^7$ are identical or different and have the following meanings:

hydrogen;

C$_1$-C$_6$-alkyl, such as methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl;

C$_3$-C$_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, in particular 2-propenyl, 2-butenyl, 3-methyl-2-butenyl or 3-methyl-2-pentenyl;

C$_3$-C$_6$-alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3- pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, preferably 2-propynyl, 2-butynyl, 1-methyl-2-propynyl or 1-methyl-2-butynyl, in particular 2-propynyl, where these alkyl, alkenyl and alkynyl groups may carry from one to five of the halogen atoms stated above in general and in particular and/or one or two of the following groups: cyano;

alkoxy of one to four carbon atoms, in particular methoxy, ethoxy, propoxy, 1-methylethoxy, butoxy, 1-methylpropoxy, 2-methylpropoxy or 1,1-dimethylethoxy, preferably methoxy, ethoxy or 1-methylethoxy;

alkenyloxy of one to four carbon atoms, in particular ethenyloxy, propenyloxy, 1-methylethenyloxy, butenyloxy, 1-methylpropenyloxy, 2-methylpropenyloxy or 1,1-dimethylethenyloxy, preferably ethenyloxy or 1-methylethenyloxy;

alkynyloxy of one to four carbon atoms, in particular ethynyloxy, propynyloxy, 1-methylethynyloxy, butynyloxy, 1-methylpropynyloxy, 2-methylpropynyloxy, 1,1-dimethylethynyloxy, preferably ethynyloxy or 1-methylethynyloxy;

alkylthio of one to four carbon atoms, in particular methylthio, ethylthio, propylthio, 1-methylethylthio, butylthio, 1-methylpropylthio, 2-methylpropylthio, 1,1-dimethylethylthio, preferably methylthio, ethylthio or 1-methylethylthio;

alkenylthio of one to four carbon atoms, in particular ethenylthio, propenylthio, 1-methylethenylthio, butenylthio, 1-methylpropenylthio, 2-methylpropenylthio, 1,1-dimethylethenylthio, preferably ethenylthio or 1-methylethenylthio;

alkynylthio of one to four carbon atoms, in particular ethynylthio, propynylthio, 1-methylethynylthio, butynylthio, 1-methylpropynylthio, 2-methylpropynylthio or 1,1-dimethylethynylthio, preferably ethynylthio or 1-methylethynylthio;

haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy, pentafluoroethoxy, in particular difluoromethoxy or trifluoromethoxy;

alkylcarbonyl, in particular methylcarbonyl, ethylcarbonyl, propylcarbonyl, 1-methylethylcarbonyl, butylcarbonyl, 1-methylpropylcarbonyl, 1,1-dimethylethylcarbonyl, pentylcarbonyl, 2-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylpropoxycarbonyl, n-pentyloxycarbonyl, 1-methylbutoxycarbonyl, 2-methylbutoxycarbonyl, 3-methylbutoxycarbonyl, 1,2-dimethylpropoxycarbonyl, 1,1-dimethylpropoxycarbonyl, 2,2-dimethylpropoxycarbonyl, 1-ethylpropoxycarbonyl, n-hexyloxycarbonyl, 1-methylpentyloxycarbonyl, 2-methylpentenyloxycarbonyl, 3-methylpentenyloxycarbonyl, 4-methylpentenyloxycarbonyl, 1,2-dimethylbutoxycarbonyl, 1,3-dimethylbutoxycarbonyl, 2,3-dimethylbutoxycarbonyl, 1,1-dimethylbutoxycarbonyl, 2,2-dimethylbutoxycarbonyl, 3,3-dimethylbutoxycarbonyl, 1,1,2-trimethylpropoxycarbonyl, 1,2,2-trimethoxypropoxycarbonyl, 1-ethylbutoxycarbonyl, 2-ethylbutoxycarbonyl, 1-ethyl-2-methylpropoxycarbonyl, n-heptyloxycarbonyl, 1-methylhexyloxycarbonyl, 2-methylhexyloxycarbonyl, 3-methylhexyloxycarbonyl, 4-methylhexyloxycarbonyl, 5-methylhexyloxycarbonyl, 1-ethylpentenyloxycarbonyl, 1-propylbutoxycarbonyl or octyloxycarbonyl, in particular methoxycarbonyl, ethoxycarbonyl, 1-methylethoxycarbonyl or 1-methylpropoxycarbonyl;

cycloalkyl, such as cyclopropyl, cyclobutyl, cyclopentyl, cyclohexyl or cycloheptyl;

dialkylamino, such as dimethylamino, diethylamino, dipropylamino, di-1-methylethyl, dibutylamino, di-1-methylpropylamino, di-2-methylpropylamino, di-1,1-dimethylethylamino, ethylmethylamino, propylmethylamino, 1-methylethylmethylamino or butylmethylamino;

phenyl, phenoxy or phenylcarbonyl, where these aromatic radicals may in turn carry from one to five halogen atoms as stated above, in particular fluorine, chlorine and bromine, and/or from one to three of the following radicals: alkyl, haloalkyl, alkoxy and/or alkylthio, each of one to four carbon atoms, as stated in general and in particular above;

substituted $C_3$–$C_{12}$-cycloalkyl, in particular $C_3$–$C_6$-cycloalkyl, such as cyclopropyl, cyclobutyl, cyclopentyl or cyclohexyl, for example 1-cyanocyclohexyl or 1-methylcyclohexyl;

phenyl which is unsubstituted or monosubstituted to trisubstituted by $C_1$–$C_4$-alkyl or $C_1$–$C_4$-alkoxy, such as methyl, ethyl, propyl, butyl, methoxy or ethoxy or phenyl which is substituted by one to five halogen atoms, e.g. chlorine or fluorine;

or $R^6$ together with $R^7$ form a $C_4$–$C_7$-alkylene chain, such as butylene, pentylene, hexylene or heptylene, which is unsubstituted or monosubstitued to tetrasubstituted by $C_1$–$C_4$-alkyl, halogen, cyano or $C_1$–$C_4$-alkoxy and in which a $CH_2$ group may be replaced with —NH, sulfur and, in particular, oxygen; examples are morpholino, piperidino and 2,6-dimethylmorpholino;

a group

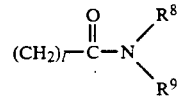

where 1 is 1, 2, 3 or 4 and $R^8$ and $R^9$ are identical or different and are each hydrogen, $C_1$–$C_6$-alkyl, $C_3$–$C_6$-alkenyl or $C_3$–$C_6$-alkynyl, each as stated above for $R^6$ and $R^7$;

a group

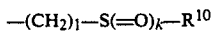

where k is 0, 1 or 2, l has the abovementioned meanings and $R^{10}$ has the meanings stated for $R^8$ or $R^9$, apart from hydrogen; or $R^1$ is a radical

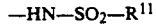

where $R^{11}$ has the following meanings:

$C_1$-$C_6$-alkyl which may carry from one to four of the following substituents: halogen, nitro, cyano or $C_1$-$C_6$-alkyl; in particular examples are methyl, cyanomethyl, ethyl, 2-nitroethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl or 1-ethyl-2-methylpropyl;

phenyl which may carry from one to four of the following substituents: halogen, nitro, cyano or $C_1$-$C_6$-alkyl; in particular examples are 2-fluorophenyl, 3-fluorophenyl, 4-fluorophenyl, 2,6-difluorophenyl, 2,4-difluorophenyl, 2,3-difluorophenyl, 2-fluoro-4-trifluoromethylphenyl, 2-chlorophenyl, 3-chlorophenyl, 2-bromophenyl, 2-iodophenyl, 2-chloro-6-fluorophenyl, 2,4-dichlorophenyl, 2,6-dichlorophenyl, 3,5-dichlorophenyl, 2-chloro-4-fluorophenyl, 2-chloro-6-methylphenyl, 2,3,5-trichlorophenyl, 2-methylphenyl, 3-methylphenyl, 4-methylphenyl, 2,6-dimethylphenyl, 2,4-dimethylphenyl, 3,5-dimethylphenyl, 2,4,6-trimethylphenyl, 2-chloro-4-methylphenyl, 2-trifluoromethylphenyl, 3-trifluoromethylphenyl, 2-cyanophenyl, 3-cyanophenyl, 4-cyanophenyl, 2-nitrophenyl, 3-nitrophenyl or 4-nitrophenyl; or a radical $OR^5$, where $R^5$ is an unsubstituted or substituted 5-membered aromatic heterocyclic structure which is bonded via a nitrogen atom and has from one to four nitrogen atoms, e.g. 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 4-iodo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl or 1-benzotriazolyl; or a group

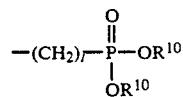

where l and $R^{10}$ have the abovementioned meanings;

$R^2$ and $R^3$ are each alkyl, e.g. methyl, ethyl, propyl, 1-methylethyl, butyl, 1-methylpropyl, 2-methylpropyl or 1,1-dimethylethyl;

haloalkyl, e.g. difluoromethyl, trifluoromethyl, chlorodifluoromethyl, dichlorofluoromethyl, 1-fluoroethyl, 2-fluoroethyl, 2,2-difluoroethyl, 1,1,2,2-tetrafluoroethyl, 2,2,2-trifluoroethyl, 2-chloro-1,1,2-trifluoroethyl, pentafluoroethyl, in particular difluoromethyl or trifluoromethyl;

alkoxy of one to four carbon atoms, in particular methoxy, ethoxy, propoxy, 1-methylethoxy, butoxy, 1-methylpropoxy, 2-methylpropoxy or 1,1-dimethylethoxy, preferably methoxy, ethoxy or 1-methylethoxy;

haloalkoxy, e.g. difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular difluoromethoxy or trifluoromethoxy;

alkylthio of one to four carbon atoms, in particular methylthio, ethylthio, propylthio, 1-methylethylthio, butylthio, 1-methylpropylthio, 2-methylpropylthio or 1,1-dimethylethylthio, preferably methylthio, ethylthio or 1-methylethylthio; and $R^4$ is hydrogen, cyano, nitro, halogen, such as fluorine, chlorine or bromine, alkyl or haloalkyl as stated for $R^2$ and $R^3$.

With regard to selective herbicidal activity, particularly preferred compounds I are those in which the substituents have the following meanings:

R is halogen, preferably chlorine or bromine, or $C_1$-$C_4$-alkyl, preferably methyl or ethyl;

$R^1$ is a radical $ONR^6R^7$, where $R^6$ and $R^7$ are each hydrogen, $C_1$-$C_4$-alkyl, a $C_4$-$C_6$-alkylene chain or a $C_3$-$C_5$-alkylene chain having a hetero atom, hydrogen, methyl, ethyl, 1,1-dimethylethyl, butylene, pentylene and 3-oxapentylene being preferred radicals;

a radical $R^5$, where $R^5$ is 1-pyrazolyl or 1-imidazolyl, or a radical $NH$—$SO_2$—$R^{11}$, where $R^{11}$ is methyl, phenyl or 4-methylphenyl;

$R^2$ and $R^3$ are each methoxy;

X is oxygen or sulfur;

Z is nitrogen or the methine group; and $R^4$ is hydrogen.

The herbicidal and growth-regulating compounds I according to the invention, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds I are generally suitable for the preparation of solutions, emulsions, pastes and oil dispersions to be sprayed direct. Examples of inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polygolycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.01 to 95, and preferably 0.5 to 90, % by weight of active ingredient. The active ingredients are used in a purity of 90 to 100, and preferably from 95 to 100, % (according to the NMR spectrum).

The compounds I according to the invention may be formulated as follows:

I. 90 parts by weight of compound no. 2.004 is mixed with 10 parts by weight of N-methyl-alpha-pyrrolidone. A mixture is obtained which is suitable for application in the form of very fine drops.

II. 20 parts by weight of compound no. 2.004 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 2.004 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 2.004 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 2.004 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 2.004 is intimately mixed with 97 parts by weight of particulate kaolin. A dust is obtained containing 3% by weight of the active ingredient.

VII. 30 parts by weight of compound no. 2.004 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 2.004 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3, preferably 0.005 to 0.5, kg of active ingredient per hectare.

The growth-regulating salicylic acid derivatives of the formula I may exercise a variety of influences on practically all plant development stages, and are therefore used as growth regulators. The diversity of action of growth regulators depends especially on a) the type and variety of plant;

b) the time applied, with reference to the development stage of the plants and the time of the year;
c) the place and method of application (seed treatment, soil treatment, application to foliage, or injection into tree trunks);
d) climatic factors, e.g., average temperature, amount of precipitation, day length and light intensity);
e) soil conditions (including fertilization);
f) the formulation of the active ingredient; and
g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height.

Of advantage in practice is for example the reduction in grass growth, and the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases.

Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The salicylic acid derivatives of the formula I may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with growth regulators. Irrigation frequency can be reduced by using the compounds according to the invention, making for lower costs, because, inter alia,
the size of the stomata opening is reduced;
a thicker epidermis and cuticle are formed;
penetration of the soil by the roots is improved;
the micro-climate in the stand is favorably influenced by the more compact growth.

The active ingredients I according to the invention may be applied not only to the seed (as a dressing), but also to the soil, i.e., via the roots, and to the foliage by spraying.

As a result of the good tolerance by crop plants, the application rate when the active ingredients are used as growth regulators may vary within wide limits.

When the active ingredients are used for treating seed, amounts of from 0.001 to 50, and preferably from 0.01 to 10, g per kg of seed are generally required. For foliage and soil treatment, amounts of from 0.001 to 10, preferably from 0.01 to 3, and especially from 0.01 to 0.5, kg/ha are generally considered to be sufficient.

The active ingredients or the herbicidal agents containing them may be applied pre- or postemergence. If certain crop plants tolerate the active ingredients less well, application techniques may be used in which the that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3, preferably 0.15 to 1.0, kg of active ingredient per hectare.

The salicylic acid derivatives of the formula I are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits, and in the seeds of these plants.

The novel compounds are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes, Alternaria species in fruit and vegetables.

The compounds are applied by treating the fungi or the plants, seeds or materials to be protected against fungus attack, or the soil with a fungicidally effective amount of the active ingredients. They may be applied before or after infection of the materials, plants or seeds by the fungi.

The fungicidal agents generally contain from 0.1 to 95, and preferably from 0.5 to 90, wt % of active ingredient.

Depending on the type of effect desired, application rates vary from 0.02 to 3 kg of active ingredient per hectare. The novel compounds may also be used for protecting materials (timber), e.g., against *Paecilomyces variotii*.

For treating seed, active ingredient amounts of from 0.001 to 50, and preferably from 0.01 to 10, g per kg of seed are generally sufficient.

The agents, or the ready-to-use formulations prepared therefrom, such as solutions, emulsions, suspensions, powders, dusts, pastes or granules, are applied in known manner, for example by spraying, atomizing, dusting, scattering, treating seed, or by watering.

To increase the spectrum of action and to achieve synergistic effects, the compounds I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexan-1,3-dione derivatives, quinolinecarboxylic acids, (hetero)-aryloxyphenoxypropionic acids and salts, esters, amides thereof, etc.

It may also be useful to apply the herbicidal compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS INSTRUCTIONS

The instructions given in the following synthesis examples may be used, after appropriate modification of the starting materials, to obtain further compounds I. The compounds thus obtained are given in the tables below with their physical data. Compounds without these data may be synthesized analogously from the corresponding starting materials. The structures given in the tables describe particularly preferred active ingredients of the formula I.

EXAMPLE 1

General Instructions for the Manufacture of Aromatic Hydroxylamine Carboxylates or Similar Compounds of the Formula I:

3.2 mmol of sodium hydride is added to 3.2 mmol of the aromatic 2-(4,6-dimethoxypyrimidin-2-yl)-oxycarboxylic acid concerned in 20 ml of dimethoxyethane. A gas immediately evolves. The mixture is stirred for 1 hour at room temperature and cooled to 0° C., and 3.5 mmol of oxalyl chloride is added. The mixture is stirred for 1 hour at 0° C., and about 30% of the solvent is evaporated under reduced pressure to remove the excess oxalyl chloride. 4.2 mmol of the hydroxylamine concerned, or a comparable hydroxy compound, dissolved in 10 ml of dimethoxyethane is added, followed by 3.2 mmol of pyridine at 0° C., and the mixture is heated at room temperature for 1 hour. The mixture is poured into 120 ml of cold water and extracted with methylene chloride. The organic phase is dried over sodium sulfate and evaporated down under reduced pressure. The substance which remains can be further purified by chromatography on silica gel.

EXAMPLE 2

General Instructions for the Manufacture of Aromatic Hydroxylamine Carboxylates or Similar Compounds of the Formula I:

1.75 g (10.8 mmol) of N,N'-carbonylbisimidazole is added to a solution of 10 mmol of the 6-aryl-2-(4,6-dimethoxypyrimidin-2-yloxy)-benzoic acid concerned in 30 ml of tetrahydrofuran. After the mixture has been stirred for 30 minutes at room temperature, 9.9 mmol of the corresponding hydroxy compound is added and the mixture stirred for a further 14 hours. The batch is then hydrolyzed with 300 ml of 1N phosphoric acid and the resulting mixture is extracted several times with methyl tert-butyl ether. The organic phases are dried over sodium sulfate and evaporated down under reduced pressure. The residue is further purified by column chromatography or recrystallization.

EXAMPLE 3

General Instructions for the Manufacture of Aromatic Hydroxylamine Carboxylates or Similar Compounds of the Formula I:

1.75 g (10.8 mmol) of N,N'-carbonylbisimidazole is added to a solution of 10 mmol of the corresponding 6-arylsalicylic acid in 30 ml of dioxane. After the mixture has been stirred for 30 minutes at room temperature, 9.9 mmol of the corresponding hydroxy compound is added and the mixture is stirred for a further 14 hours. The reaction mixture is then hydrolyzed with 300 ml of 1N phosphoric acid and then extracted several times with methyl tert-butyl ether. The organic phases are combined, dried over sodium sulfate and evaporated down under reduced pressure. The residue is taken up with 40 ml of dimethylformamide and 280 mg of sodium hydride (85% in paraffin, 10 mmol) is added. After the mixture has been stirred for 30 minutes at room temperature, 1.97 g (9 mmol) of 4,6-dimethoxy-2-methylsulfonylpyrimidine is added and the resulting mixture is stirred for 14 hours. The mixture is introduced into 300 ml of 0.1N phosphoric acid and extracted with diethyl ether. The ether phase is dried over sodium sulfate and evaporated down, and the residue is purified by column chromatography or recrystallization.

EXAMPLE 4

At 10° C., 0.46 g (0.015 mol) of sodium hydride (80% strength) is added to a solution of 15 mmol of azolyl 6-arylsalicylate in 25 ml of dried dimethylformamide, and the mixture is stirred for 3 hours at 30° C. 3.27 g (0.015 mol) of 2-methylsulfonyl-4,6-dimethoxypyrimidine is added and the mixture stirred for 12 hours at room temperature. The reaction mixture is introduced into 500 ml of water to which 2.5 ml of orthophosphoric acid has previously been added. The oil which separates out is taken up in ethyl acetate and dried over sodium sulfate. The residue remaining after evaporation is purified by column chromatography or recrystallization.

EXAMPLE 5

6-(4-Bromophenyl)-2-(4,6-dimethoxypyrimidin-2-yloxy)-1-(N,N-dimethylaminooxycarbonyl)-benzene (Example 2.004)

At 10° C., 0.30 g (0.01 mol) of sodium hydride (80% strength) is added to a solution of 3.35 g (10 mmol) of 3-(4-bromophenyl)-2-(N,N-dimethylaminooxycarbonyl)-phenol in 25 ml of dried dimethylformamide, and the mixture is stirred for 3 hours at 30° C. Subsequently, 2.18 g (0.01 mol) of 2-methylsulfonyl-4,6-dimethoxypyrimidine is added and the mixture stirred for 12 hours at room temperature. Working up in accordance with Example 4 gives a colorless solid.

EXAMPLE 6

6-(4-Chlorophenyl)-2-(4,6-dimethoxypyrimidin-2-yloxy)-1-(N,N-dimethylaminooxycarbonyl)-benzene (Example 2.003)

3.2 mmol of sodium hydride is added to 1.24 g (3.2 mmol) of 6-(4-chlorophenyl)-2-(4,6-dimethoxypyrimidin-2-yl)-benzoic acid in 20 ml of dimethoxyethane; a gas immediately evolves. The mixture is stirred for 1 hour at room temperature and cooled to 0° C., and 3.5 mmol of oxalyl chloride is added. The mixture is stirred for 1 hour at 0° C. and about 30% of the solvent is evaporated under reduced pressure to remove the excess oxalyl chloride. A solution of 4.2 mmol of N,N-dimethylhydroxylamine in 10 ml of dimethoxyethane (from 230 mg of N,N-dimethylhydroxylamine hydrochloride and 332 mg of pyridine) and then 3.2 mmol of pyridine are then added at 0° C., and the mixture is heated to room temperature over a period of 1 hour. The mixture is poured into 120 ml of cold water and extracted with methylene chloride. The organic phase is dried over sodium sulfate and evaporated down under reduced pressure. The oil which remains is further purified by chromatography on silica gel.

EXAMPLE 7

6-(2-Methylphenyl)-2-(3,5-dimethoxy-s-triazin-1-yloxy)-1-[(1-pyrazolyl)-oxycarbonyl]-benzene (Example 1.022)

1.75 g (10.8 mmol) of N,N'-carbonylbisimidazole is added to a solution of 2.12 g (10 mmol) of 6-(2-methylphenyl)-salicylic acid in 30 ml of tetrahydrofuran. After the mixture has been stirred for 30 minutes at room temperature 9.9 mmol of N-hydroxypyrazole is added and the mixture is stirred for a further 14 hours. The mixture is then hydrolyzed with 300 ml of 1N phosphoric acid and extracted several times with methyl tert-butyl ether. The organic phases are combined, dried over sodium sulfate and evaporated down under reduced pressure. The residue is taken up with 40 ml of dimethylformamide and 280 mg of sodium hydride (85% strength in paraffin, 10 mmol) is added. After the mixture has been stirred for 30 minutes at room temperature, 1.58 g (9 mmol) of 1-chloro-3,5-dimethoxy-s-triazine is added and the mixture stirred for 14 hours. It is then introduced into 300 ml of 0.1N phosphoric acid and extracted with diethyl ether. The ether phase is dried over sodium sulfate and evaporated down, and the residue is purified by column chromatography.

TABLE 1

Compounds in which $R^1$ is a radical $OR^5$ (I)

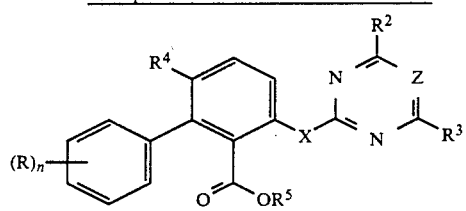

| No. | $R^5$ | $R^2$ | $R^3$ | $R^4$ | X | Z | (R)m | Phys. data |
|---|---|---|---|---|---|---|---|---|
| 1.001 | 1-Pyrazolyl | $OCH_3$ | $OCH_3$ | H | O | CH | all-H | |
| 1.002 | 1-Pyrazolyl | $OCH_3$ | $OCH_3$ | H | O | N | all-H | |
| 1.003 | $CH_2-P(O)(OC_2H_5)_2$ | $OCH_3$ | $OCH_3$ | H | O | CH | all-H | |
| 1.004 | 3-Methyl-1-pyrazolyl | $OCH_3$ | $OCH_3$ | H | O | CH | all-H | |
| 1.005 | 4-Chloro-1-pyrazolyl | $OCH_3$ | $OCH_3$ | H | O | CH | all-H | |
| 1.006 | 1-Imidazolyl | $OCH_3$ | $OCH_3$ | H | O | CH | all-H | |
| 1.007 | 1-Triazolyl | $OCH_3$ | $OCH_3$ | H | O | CH | all-H | |
| 1.008 | 1-Pyrazolyl | $OCH_3$ | $OCH_3$ | H | O | CH | 4-Br | |
| 1.009 | $CH_2-P(O)(OC_2H_5)_2$ | $OCH_3$ | $OCH_3$ | H | O | CH | 4-Br | |
| 1.010 | 3-Methyl-1-pyrazolyl | $OCH_3$ | $OCH_3$ | H | O | CH | 4-Br | |
| 1.011 | 4-Chloro-1-pyrazolyl | $OCH_3$ | $OCH_3$ | H | O | CH | 4-Br | |
| 1.012 | 1-Imidazolyl | $OCH_3$ | $OCH_3$ | H | O | CH | 4-Br | |
| 1.013 | 1-Triazolyl | $OCH_3$ | $OCH_3$ | H | O | CH | 4-Br | |
| 1.014 | 1-Pyrazolyl | $OCH_3$ | $OCH_3$ | H | O | CH | 4-Cl | |
| 1.015 | 1-Pyrazolyl | $OCH_3$ | $OCH_3$ | H | O | N | 4-Cl | |
| 1.016 | $CH_2-P(O)(OC_2H_5)_2$ | $OCH_3$ | $OCH_3$ | H | O | CH | 4-Cl | |
| 1.017 | 3-Methyl-1-pyrazolyl | $OCH_3$ | $OCH_3$ | H | O | CH | 4-Cl | |
| 1.018 | 4-Chloro-1-pyrazolyl | $OCH_3$ | $OCH_3$ | H | O | CH | 4-Cl | |
| 1.019 | 1-Imidazolyl | $OCH_3$ | $OCH_3$ | H | O | CH | 4-Cl | |
| 1.020 | 1-Triazolyl | $OCH_3$ | $OCH_3$ | H | O | CH | 4-Cl | |
| 1.021 | 1-Pyrazolyl | $OCH_3$ | $OCH_3$ | H | O | CH | 2-$CH_3$ | |
| 1.021 | 1-Pyrazolyl | $OCH_3$ | $OCH_3$ | H | O | N | 2-$CH_3$ | |
| 1.023 | $CH_2-P(O)(OC_2H_5)_2$ | $OCH_3$ | $OCH_3$ | H | O | CH | 2-$CH_3$ | |
| 1.024 | 3-Methyl-1-pyrazolyl | $OCH_3$ | $OCH_3$ | H | O | CH | 2-$CH_3$ | |
| 1.025 | 4-Chloro-1-pyrazolyl | $OCH_3$ | $OCH_3$ | H | O | CH | 2-$CH_3$ | |
| 1.026 | 1-Imidazolyl | $OCH_3$ | $OCH_3$ | H | O | CH | 2-$CH_3$ | |
| 1.027 | 1-Triazolyl | $OCH_3$ | $OCH_3$ | H | O | CH | 2-$CH_3$ | |

TABLE 1-continued

Compounds in which $R^1$ is a radical $OR^5$

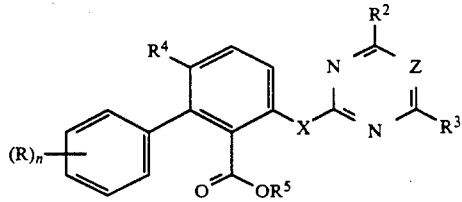

(I)

| No. | $R^5$ | $R^2$ | $R^3$ | $R^4$ | X | Z | (R)m | Phys. data |
|---|---|---|---|---|---|---|---|---|
| 1.028 | 1-Pyrazolyl | $OCH_3$ | $OCH_3$ | H | S | CH | all-H | |
| 1.029 | $CH_2-P(O)(OC_2H_5)_2$ | $OCH_3$ | $OCH_3$ | H | S | CH | all-H | |
| 1.030 | 1-Pyrazolyl | $OCH_3$ | $OCH_3$ | H | S | CH | 4-Br | |
| 1.031 | 1-Imidazolyl | $OCH_3$ | $OCH_3$ | H | S | CH | 4-Br | |
| 1.032 | 1-Pyrazolyl | $OCH_3$ | $OCH_3$ | H | S | CH | 4-Cl | |
| 1.033 | 1-Pyrazolyl | $OCH_3$ | $OCH_3$ | H | S | CH | 2-$CH_3$ | |

TABLE 2

Compounds in which $R^1$ is a radical $O-NR^6R^7$

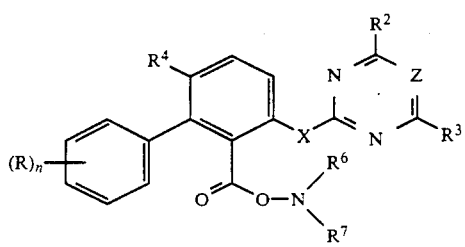

(I)

| No. | $R^6$ | $R^7$ | $R^2$ | $R^3$ | $R^4$ | X | Z | (R)m | Phys. data |
|---|---|---|---|---|---|---|---|---|---|
| 2.001 | $CH_3$ | CH3 | $OCH_3$ | $OCH_3$ | H | S | CH | all-H | |
| 2.002 | $CH_3$ | CH3 | $OCH_3$ | $OCH_3$ | H | O | N | all-H | |
| 2.003 | $CH_3$ | CH3 | $OCH_3$ | $OCH_3$ | H | O | CH | 4-Cl | 116–124 |
| 2.004 | $CH_3$ | CH3 | $OCH_3$ | $OCH_3$ | H | O | CH | 4-Br | 130–135 |
| 2.005 | $CH_3$ | CH3 | $OCH_3$ | $OCH_3$ | H | S | CH | 4-Cl | |
| 2.006 | $CH_3$ | CH3 | $OCH_3$ | $OCH_3$ | H | S | CH | 4-Br | |
| 2.007 | $CH_3$ | CH3 | $OCH_3$ | $OCH_3$ | H | O | N | 4-Cl | |
| 2.008 | $CH_3$ | CH3 | $OCH_3$ | $OCH_3$ | H | O | N | 4-Br | 87–155 |
| 2.009 | $CH_3$ | CH3 | $OCH_3$ | $OCH_3$ | H | O | CH | 2-$CH_3$ | |
| 2.010 | H | t-C4H9 | $OCH_3$ | $OCH_3$ | H | O | CH | all-H | |
| 2.011 | H | t-C4H9 | $OCH_3$ | $OCH_3$ | H | O | CH | 4-Cl | |
| 2.012 | H | t-C4H9 | $OCH_3$ | $OCH_3$ | H | O | CH | 4-Br | 117–119 |
| 2.013 | H | t-C4H9 | $OCH_3$ | $OCH_3$ | H | O | CH | 2-$CH_3$ | |
| 2.014 | $-CH_2(CH_2)_3CH_2-$ | | $OCH_3$ | $OCH_3$ | H | O | CH | all-H | |
| 2.015 | $-CH_2(CH_2)_3CH_2-$ | | $OCH_3$ | $OCH_3$ | H | O | CH | 4-Cl | |
| 2.016 | $-CH_2(CH_2)_3CH_2-$ | | $OCH_3$ | $OCH_3$ | H | O | CH | 4-Br | |
| 2.017 | $-CH_2(CH_2)_3CH_2-$ | | $OCH_3$ | $OCH_3$ | H | O | CH | 2-$CH_3$ | |
| 2.018 | $-(CH_2)_2O(CH_2)_2-$ | | $OCH_3$ | $OCH_3$ | H | O | CH | all-H | |
| 2.019 | $-(CH_2)_2O(CH_2)_2-$ | | $OCH_3$ | $OCH_3$ | H | O | CH | 4-Cl | |
| 2.020 | $-(CH_2)_2O(CH_2)_2-$ | | $OCH_3$ | $OCH_3$ | H | O | CH | 4-Br | |
| 2.021 | $-(CH_2)_2O(CH_2)_2-$ | | $OCH_3$ | $OCH_3$ | H | O | CH | 2-$CH_3$ | |
| 2.022 | H | $CH_3$ | $OCH_3$ | $CH_3$ | H | O | CH | all-H | |
| 2.023 | H | $CH_3$ | $OCH_3$ | $OCH_3$ | H | O | CH | 4-Cl | |
| 2.024 | H | $CH_3$ | $OCH_3$ | $OCH_3$ | H | O | CH | 4-Br | |
| 2.025 | H | $CH_3$ | $OCH_3$ | $OCH_3$ | H | O | CH | 2-$CH_3$ | |

TABLE 3

Compounds I in which $R^1$ is a radical $O-NH-SO_2-R^{11}$

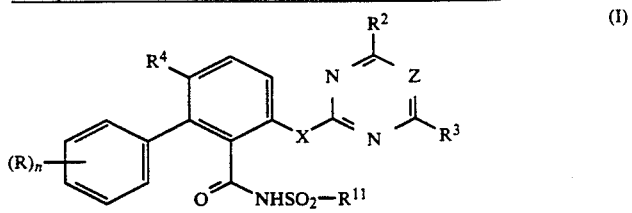

(I)

| No. | (R)m | $R^{11}$ | $R^2$ | $R^3$ | $R^4$ | X | Z | Phys. data mp. [°C.] |
|---|---|---|---|---|---|---|---|---|
| | | | | | | | | Phys. data |
| 3.001 | all-H | $CH_3$ | $OCH_3$ | $OCH_3$ | H | O | CH | |
| 3.002 | all-H | $CH_3$ | $OCH_3$ | $OCH_3$ | H | S | CH | |
| 3.003 | all-H | $CH_3$ | $OCH_3$ | $OCH_3$ | H | O | N | |
| 3.004 | all-H | $C_6H_5$ | $OCH_3$ | $OCH_3$ | H | O | CH | |
| 3.005 | all-H | $C_6H_4$-4-$CH_3$ | $OCH_3$ | $OCH_3$ | H | O | CH | |
| 3.006 | 4-Br | $CH_3$ | $OCH_3$ | $OCH_3$ | H | O | CH | |
| 3.007 | 4-Br | $C_6H_4$-4-$CH_3$ | $OCH_3$ | $OCH_3$ | H | O | CH | |
| 3.008 | 4-Cl | $CH_3$ | $OCH_3$ | $OCH_3$ | H | O | CH | |
| 3.009 | 4-Cl | $C_6H_4$-4-$CH_3$ | $OCH_3$ | $OCH_3$ | H | O | CH | |
| 3.010 | 2-$CH_3$ | $CH_3$ | $OCH_3$ | $OCH_3$ | H | O | CH | |
| 3.011 | 2-$CH_3$ | $C_6H_4$-4-$CH_3$ | $OCH_3$ | $OCH_3$ | H | O | CH | |

The herbicidal action of salicylic acid derivatives of the formula I according to the invention is demonstrated in greenhouse experiments:

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, plants were used which had been sown in the pots and grown there, or they were grown separately as seedlings and transplanted to the pots a few days before treatment. The plants were grown, depending on growth form, to a height of 3 to 15 cm before being treated with the compounds, suspended or emulsified in water. The application rates for postemergence treatment were 0.03 and 0.015 kg/ha.

The pots were set up in the greenhouse, heat-loving species at from 20° to 35° C., and species from moderate climates at from 10° to 25° C. The experiments were run for from 2 to 4 weeks. During this period the plants were tended and their reactions to the various treatments assessed.

The assessment scale was 0 to 100, 100 denoting nonemergence or complete destruction of at least the visible plant parts, and 0 denoting no damage or normal growth.

The plants used in the greenhouse experiments were as follows:

| Abbreviation | Botanical name | Common name |
|---|---|---|
| HORVS | *Hordeum vulgare* | spring barley |
| TRZAS | *Triticum aestivum* | spring wheat |
| ALOMY | *Alopecurus myosuroides* | blackgrass |
| STEME | *Stellaria media* | chickweed |
| SOLNI | *Solanum nigrum* | black nightshade |

The following comparative experiment between compound 2.004 and compound no. 44 from EP-A 426 476 (comparative compound A) demonstrates the surprisingly high selectivity of the compounds according to the invention in spring barley and spring wheat, combined with excellent herbicidal action. In view of the intolerably high damage caused, comparative compound A cannot be used in these crops.

The results are set forth in Table I.

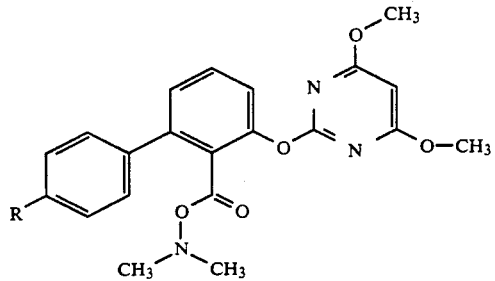

TABLE I

Examples demonstrating the control of injurious grasses and weeds and tolerance by crop plants on postemergence application of 0.03 and 0.015 kg/ha in the greenhouse

| Ex. No. | 2.004 | | A | |
|---|---|---|---|---|
| R | Br | | H | |
| kg/ha | 0.03 | 0.015 | 0.03 | 0.015 |
| Test plants | Damage in % | | | |
| HORVS cv. Alexis | 0 | 0 | 60 | 50 |
| TRZAS cv. Star | 20 | 0 | 90 | 90 |
| ALOMY | 95 | 95 | 95 | 95 |

TABLE I-continued

Examples demonstrating the control of injurious grasses and weeds and tolerance by crop plants on postemergence application of 0.03 and 0.015 kg/ha in the greenhouse

| | | | | |
|---|---|---|---|---|
| STEME | 100 | 98 | 100 | 98 |
| SOLNI | 98 | 90 | 98 | 85 |

We claim:

1. A salicylic acid derivative or a sulfur analog thereof of the formula I

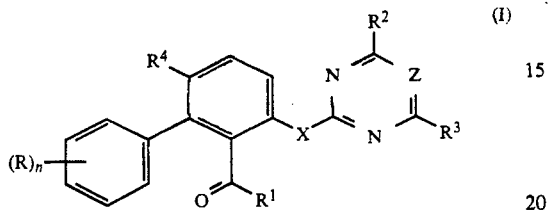

where
R is halogen,
n is 1, 2 or 3 or, in the case of halogen as substituents, 1, 2, 3, 4 or 5;
$R^1$ is a radical

where m is 0 or 1 and $R^6$ and $R^7$ have the following meanings:
hydrogen;
$C_1$-$C_6$-alkyl, $C_3$-$C_6$-alkenyl or $C_3$-$C_6$-alkynyl, where these radicals may each carry from one to five halogen atoms or one or two of the following groups: $C_1$-$C_6$-alkoxy, $C_3$-$C_6$-alkenyloxy, $C_3$-$C_6$-alkynyloxy, $C_1$-$C_6$-alkylthio, $C_3$-$C_6$-alkenylthio, $C_3$-$C_6$-alkynylthio, $C_1$-$C_6$-haloalkoxy, cyano, $C_1$-$C_6$-alkylcarbonyl, $C_3$-$C_6$-alkenylcarbonyl, $C_3$-$C_6$-alkynylcarbonyl, $C_1$-$C_6$-alkoxycarbonyl, $C_3$-$C_6$-alkenyloxycarbonyl, $C_3$-$C_6$-alkynyloxycarbonyl, bis-$C_1$-$C_6$-dialkylamino, $C_3$-$C_6$-cycloalkyl or unsubstituted or substituted phenyl;
unsubstituted or substituted $C_3$-$C_6$-cycloalkyl;
unsubstituted or substituted phenyl; or
$R^6$ together with $R^7$ forms a morpholino, piperidino or 2,6-dimethylmorpholino group; or
$R^1$ is a group

where $R^8$ and $R^9$ are each hydrogen, $C_1$-$C_6$-alkyl, $C_3$-$C_6$-alkenyl or $C_3$-$C_6$-alkynyl and l is 1, 2, 3 or 4; or
$R^1$ is a group

where $R^{10}$ is a $C_1$-$C_6$-alkyl, $C_3$-$C_6$-alkenyl or $C_3$-$C_6$-alkynyl, l is 1, 2, 3 or 4 and k is 0, 1 or 2; or
$R^1$ is a radical

—HN—$SO_2$—$R^{11}$ where $R^{11}$ is a $C_1$-$C_6$-alkyl or phenyl which in turn may carry from one to four of the following substituents: halogen, nitro, cyano or $C_1$-$C_6$-alkyl; or
$R^1$ is a radical $OR^5$, where $R^5$ is an unsubstituted or substituted 5-membered aromatic heterocyclic structure selected from the group consisting of 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 4-iodo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl or 1-benzotriazolyl; or
$R^1$ is a radical

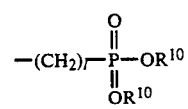

where $R^{10}$ and l have the abovementioned meanings, the expression unsubstituted or substituted in the above definitions meaning that the group designated in this manner can be either unsubstituted or carry one or more of the following substituents: halogen, nitro, cyano, $C_1$-$C_6$-alkyl, $C_1$-$C_6$-haloalkyl, $C_1$-$C_6$-alkoxy or $C_1$-$C_6$-alkylthio;
$R^2$ and $R^3$ are each $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio;
$R^4$ is hydrogen, halogen, nitro, $C_1$-$C_4$-alkyl, cyano or $C_1$-$C_4$-haloalkyl;
X is oxygen or sulfur, and
Z is the methine group.

2. A salicylic acid derivative of the formula I as defined in claim 1, where $R^1$ is O—$N(CH_3)_2$, X is oxygen, Y is nitrogen, Z is the methine group, $R^2$ and $R^3$ are each methoxy and (R) is 4-Cl or 4-Br.

3. A herbicidal composition containing a compound of the formula I as defined in claim 1 and conventional inert additives.

4. A method for controlling undesirable plant growth, wherein the undesirable plants or their habitat is or are treated with a herbicidal amount of a compound I as defined in claim 1.

5. A method for regulating plant growth, wherein an amount, having a regulatory action, of a salicylic acid derivative of the formula I as defined in claim 1 is allowed to act on the seeds, the plants or their habitat.

6. A salicylic acid derivative or a sulfur analog thereof of the formula I

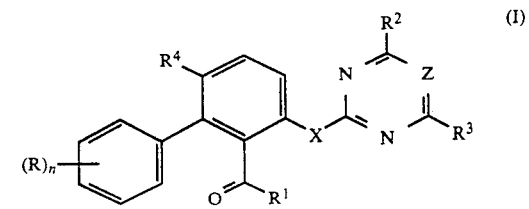

where
R is halogen
n is 1, 2 or 3,
$R^1$ is a radical

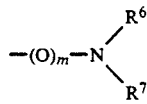

where m is 0 or 1 and $R^6$ and $R^7$ have the following meanings:

halogen;

$C_1$–$C_6$-alkyl, $C_3$–$C_6$-alkenyl or $C_3$–$C_6$-alkynyl, where these radicals may each carry from one to five halogen atoms or one or two of the following groups: $C_1$–$C_6$-alkoxy, $C_3$–$C_6$-alkenyloxy, $C_3$–$C_6$-alkynyloxy, $C_1$–$C_6$-alkylthio, $C_1$–$C_6$-haloalkoxy, cyano, $C_1$–$C_6$-alkylcarbonyl, $C_3$–$C_6$-alkenylcarbonyl, $C_3$–$C_6$-alkynylcarbonyl, $C_1$–$C_6$-alkoxycarbonyl, $C_3$–$C_6$-alkenyloxycarbonyl, $C_3$–$C_6$-alkynyloxycarbonyl, bis-$C_1$–$C_6$-dialkylamino, $C_3$–$C_6$-cycloalkyl or unsubstituted or substituted phenyl;

unsubstituted or substituted phenyl; or $R^6$ together with $R^7$ forms a morpholine, piperidino or 2,6-dimethylmorpholiine group;

X is oxygen or sulfur, and

Z is the methine group.

7. A compound of the formula I as defined in claim 1, wherein $(R)_n$ is 4-Br and $R^6$ and $R^7$ are each methyl.

8. A compound of the formula I as defined in claim 1, wherein $(R)_n$ is 4-Br, $R^6$ and $R^7$ are each methyl and $R^2$ and $R^3$ are each methoxy.

9. A method for controlling undesirable plant growth, wherein the undesirable plants or their habitat are treated with a herbicidal amount of a compound I as defined in claim 7.

10. A method for controlling undesirable plant growth, wherein the undesirable plants or their habitat are treated with a herbicidal amount of a compound I as defined in claim 8.

* * * * *

UNITED STATES PATENT AND TRADEMARK OFFICE
CERTIFICATE OF CORRECTION

PATENT NO. : 5,290,755
DATED : March 1, 1994
INVENTOR(S) : VOGELBACHER et al.

It is certified that error appears in the above-indentified patent and that said Letters Patent is hereby corrected as shown below:

Title Page:
In the Abstract, last line, after the period insert the following sentence:
--These compounds have been shown to be useful as selective herbicides.--

Claim 1, column 21, line 55, in the formula, "-$(CH_2)_1$-" should be -- -$(CH_2)_\ell$- --.

Claim 1, column 21, line 59, " $C_3$-$C_6$-alkynyl and 1" should be -- $C_3$-$C_6$-alkynyl and $\ell$ --.

Claim 1, column 21, line 63, in the formula, "-$(CH_2)_1$-" should be -- -$(CH_2)_\ell$- --.

Claim 1, column 21, line 66, "1 is 1" should be --$\ell$ is 1--.

Claim 1, column 21, line 66, "o" should be --0--.

UNITED STATES PATENT AND TRADEMARK OFFICE
CERTIFICATE OF CORRECTION

PATENT NO. : 5,290,755
DATED : March 1, 1994
INVENTOR(S) : VOGELBACHER et al.

It is certified that error appears in the above-indentified patent and that said Letters Patent is hereby corrected as shown below:

Claim 1, column 22, line 20, in the formula, "-$(CH_2)_1$-" should be -- -$(CH_2)_2$- --.

Claim 1, column 22, line 23, "1" should be --$l$--.

Claim 6, column 24, line 4, "morpholine" should be --morpholino--.

Claim 6, column 24, line 5, "2,6-dimethylmorpholiine" should be --2,6-dimethylmorpholino--.

Signed and Sealed this

Twentieth Day of September, 1994

Attest:

BRUCE LEHMAN

*Attesting Officer*  *Commissioner of Patents and Trademarks*